(12) United States Patent
Tabata et al.

(10) Patent No.: US 9,375,231 B2
(45) Date of Patent: Jun. 28, 2016

(54) EXCISION DEVICE AND AIR-BUBBLE DETECTING METHOD

(71) Applicant: SEIKO EPSON CORPORATION, Tokyo (JP)

(72) Inventors: Kunio Tabata, Shiojiri (JP); Takahiro Matsuzaki, Shiojiri (JP); Shinichi Miyazaki, Suwa (JP); Takeshi Seto, Chofu (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/481,752

(22) Filed: Sep. 9, 2014

(65) Prior Publication Data

US 2014/0379013 A1 Dec. 25, 2014

Related U.S. Application Data

(63) Continuation of application No. 13/035,156, filed on Feb. 25, 2011, now abandoned.

(30) Foreign Application Priority Data

Mar. 1, 2010 (JP) .................................. 2010-043861

(51) Int. Cl.
*A61B 17/3203* (2006.01)
*A61B 17/00* (2006.01)

(52) U.S. Cl.
CPC ... *A61B 17/3203* (2013.01); *A61B 2017/00039* (2013.01); *A61B 2017/00119* (2013.01)

(58) Field of Classification Search
CPC ........... A61B 17/3203; A61B 17/3205; A61B 17/32056; A61B 2017/00039; A61B 2017/00119; A61B 17/0011
See application file for complete search history.

(56) References Cited

U.S. PATENT DOCUMENTS

| 4,518,974 A * | 5/1985 | Isayama ..................... B41J 2/19 347/92 |
| 4,625,220 A * | 11/1986 | Nagashima .............. B41J 2/165 310/317 |
| 5,500,657 A | 3/1996 | Yauchi et al. |
| 6,257,694 B1 | 7/2001 | Tokumaru et al. |
| 6,375,299 B1 | 4/2002 | Foster et al. |

(Continued)

FOREIGN PATENT DOCUMENTS

| EP | 1-905-590 | 4/2008 |
| EP | 2-039-515 | 3/2009 |

(Continued)

OTHER PUBLICATIONS

European Search Report for Application No. 11155967.0 dated Jun. 10, 2015.

*Primary Examiner* — Jocelin Tanner
(74) *Attorney, Agent, or Firm* — Workman Nydegger (57) ABSTRACT

An excision device configured to excise living tissue by ejecting liquid includes: a supplying unit configured to supply liquid to be ejected; a chamber configured to be filled with the supplied liquid; an ejection nozzle connected to the chamber; a drive member configured to be deformed in the direction to reduce the volume of the chamber when a drive voltage is applied more than a case where the drive voltage is not applied; a liquid ejecting unit configured to eject the liquid in the chamber in a pulsed manner from the ejection nozzle by applying the drive voltage to the drive member in a state in which the chamber is filled with the supplied liquid; and an air-bubble detecting unit configured to detect air bubbles in the chamber by detecting an electric current flowing in the drive member when the drive voltage is applied to the drive member.

6 Claims, 9 Drawing Sheets

(56) References Cited

U.S. PATENT DOCUMENTS

| | | |
|---|---|---|
| 7,588,308 B2 | 9/2009 | Ootsuka |
| 2004/0058438 A1* | 3/2004 | Fujii ................. G01N 35/1074 435/309.1 |
| 2007/0103500 A1 | 5/2007 | Ootsuka |
| 2008/0086077 A1* | 4/2008 | Seto ................... A61B 17/3203 604/48 |

FOREIGN PATENT DOCUMENTS

| | | |
|---|---|---|
| JP | 05-131634 | 5/1993 |
| JP | 06-297726 | 10/1994 |
| JP | 11-099646 | 4/1999 |
| JP | 11-334102 | 12/1999 |
| JP | 2001-132646 | 5/2001 |
| JP | 2003-118093 | 4/2003 |
| JP | 2004-009501 | 1/2004 |
| JP | 2005-152127 | 6/2005 |
| JP | 2006-231882 | 9/2006 |
| JP | 2007-90654 | 4/2007 |
| JP | 2008-82202 | 4/2008 |

* cited by examiner

EXCISION DEVICE AND AIR-BUBBLE DETECTING METHOD

CROSS-REFERENCE TO RELATED APPLICATIONS

This application is a continuation application of U.S. patent application Ser. No. 13/035,156, filed Feb. 25, 2011, which patent application is incorporated herein by reference in its entirety. U.S. patent application Ser. No. 13/035,156 claims the benefit of Japanese Patent Application No. 2010-043861, filed on Mar. 1, 2010, the contents of which is hereby incorporated by reference in its entirety.

BACKGROUND

1. Technical Field

The present invention relates to a technology for incising or excising living tissue by ejecting pressurized liquid toward the living tissue.

2. Related Art

A technology for incising or excising tissue or the like by pressurizing liquid such as water or physiologic saline and ejecting the liquid from an ejection nozzle toward the living tissue in a restricted state is developed (JP-A-2005-152127). This technology enables incision of tissue such as internal organ exclusively without damaging vascular structures such as blood vessels, and causes less damage to peripheral tissues. Therefore, burdens on patients can be reduced.

There is also proposed a technology configured to eject a pulsed jet stream intermittently when ejecting liquid instead of ejecting continuously from an ejection nozzle. In this proposed technology, liquid is supplied to a small liquid chamber connected to the ejection nozzle and reduces the volume of the liquid chamber instantaneously, thereby ejecting liquid from the ejection nozzle in a pulsed manner. Subsequently, the volume of the liquid chamber is restored and the liquid is supplied again. By repeating such actions, the pulsed jet stream is ejected intermittently. In this manner, by ejecting the pulsed jet stream, the pressure of the jet stream is impulsively applied to the living tissue, and hence the living tissue can be incised with a small amount of ejection. Consequently, such events that the visibility of the living tissue to be incised is lowered due to the ejected liquid accumulated therearound or the force of the jet stream is damped by the accumulated liquid and hence the incising capability is lowered can be restrained (JP-A-2008-082202).

However, in the technology for ejecting the liquid in a pulsed manner, there is a problem such that keeping the stable incising capability is difficult. In other words, since the pulsed jet stream is ejected by pressurizing the liquid by reducing the volume of the liquid chamber instantaneously, if air bubbles get into the liquid chamber, the air bubbles are compressed, and hence the liquid cannot be pressurized sufficiently. Consequently, the incising capability is lowered. When the jet stream is apparently slowed due to too many air bubbles trapped therein, the incising capability may be restored by removing the trapped air bubbles. However, when the quantity of bubbles got into the liquid chamber is small, an operator cannot recognize that the air bubbles are trapped and hence continues to use the device with the lowered incising capability.

SUMMARY

An advantage of some aspects of the invention is to provide a technology which enables trapped air bubbles to be detected with high degree of accuracy and immediately even though the quantity of the trapped air bubbles is small for a device which is used for incising or excising living tissue by ejecting pulsed liquid.

According to an aspect of the invention, there is provided a an excision device configured to excise living tissue by ejecting liquid toward the living tissue including a liquid supplying unit configured to supply liquid to be ejected, a liquid chamber configured to be filled with the supplied liquid, an ejection nozzle connected to the liquid chamber, a drive member configured to be deformed in the direction to reduce the volume of the liquid chamber when a drive voltage is applied more than a case where the drive voltage is not applied, a liquid ejecting unit configured to eject the liquid in the liquid chamber in a pulsed manner from the ejection nozzle by applying the drive voltage to the drive member in a state in which the liquid chamber is filled with the supplied liquid, and an air-bubble detecting unit configured to detect air bubbles in the liquid chamber by detecting an electric current flowing in the drive member when the drive voltage is applied to the drive member.

In this configuration, the liquid in the liquid chamber can be pressurized and ejected from the ejection nozzle by applying the drive voltage to the drive member in a state in which the liquid chamber is filled with the liquid. If the air bubbles are trapped in the liquid chamber at this time, the trapped air bubbles are crushed by the application of the drive voltage to the drive member. Therefore, when comparing with the case where the air bubbles are not trapped, the state of deformation of the drive member is varied and, consequently, the current waveform flowing in the drive member is also varied according to the presence or absence of the trapped air bubbles. Accordingly, the presence or absence of the air bubbles trapped in the liquid chamber is detected by detecting an electric current flowing in the drive member when the drive voltage is applied to the drive member.

Accordingly, even when a small quantity of the air bubbles is trapped, immediate detection is possible. Provision of a specific device for detecting the air bubbles is not necessary because what is necessary is just to detect the electric current flowing in the drive member when the drive voltage is applied to the drive member for ejecting the liquid, so that the air bubbles can be detected very easily. In addition, since the specific device for detecting the air bubbles is not necessary, the excision device is not upsized, and hence the workability when incising or excising the living tissue is not deteriorated.

The air-bubble detecting unit may be configured to detect the air bubbles in the liquid chamber by detecting a peak current of the electric current flowing in the driving member.

When the air bubbles get into the liquid chamber, the variations of the electric current flowing in the drive member characteristically appear in the peak current. Therefore, the presence or absence of the air bubbles trapped in the liquid chamber can be detected easily with high degree of accuracy by detecting the peak current.

In the excision device described above, the air bubbles in the liquid chamber may be detected in the following manner. First of all, when ejecting the liquid, a drive voltage having a waveform rising to a predetermined maximum voltage and then lowering from the maximum voltage is applied to the drive member. The air bubbles trapped in the liquid chamber may be detected by detecting an electric current flowing in the drive member at a timing when the maximum voltage is applied to the drive member.

When ejecting the liquid, if the drive voltage having a waveform rising to the predetermined maximum voltage and then lowering from the maximum voltage is applied to the drive member, an electric current flowing to the drive member at the timing when the maximum voltage is applied is characteristically varied depending on the presence or absence of the air bubbles trapped in the liquid chamber. Therefore, the presence or absence of the air bubbles trapped in the liquid chamber can be detected easily with high degree of accuracy by detecting the electric current at this timing.

The air-bubble detecting unit may be configured to detect the air bubbles in the liquid chamber by comparing the electric current flowing in the drive member with the reference current stored according to the drive member.

The fact that the electric current flowing in the drive member has an individual difference from one driving member to another when the voltage is applied to the drive member in a state in which the air bubbles are trapped in the liquid chamber is known from the experience. Therefore, by storing the reference current adequate according to the drive member in advance and comparing the electric current flowing in the drive member with the reference current according to the drive member, the air bubbles in the liquid chamber can be detected with high degree of accuracy without being affected by the individual difference of the drive member.

According to another aspect of the invention, the invention may be implemented as an air-bubble detecting method for detecting the air bubbles in the liquid chamber by being applied to the device configured to excise the living tissue by ejecting the liquid toward the living tissue. That is, there is provided an air-bubble detecting method applied to an excision device including a liquid chamber configured to be filled with liquid to be ejected toward living tissue, an ejection nozzle connected to the liquid chamber, and a drive member configured to be deformed in the direction to reduce the volume of the liquid chamber when a drive voltage is applied more than a case where the drive voltage is not applied for detecting air bubbles in the liquid chamber, including supplying the liquid to the interior of the liquid chamber, ejecting the liquid in the liquid chamber from the ejection nozzle by applying the drive voltage to the drive member in a state in which the liquid chamber is filled with the liquid, and detecting air bubbles in the liquid chamber by detecting an electric current flowing in the drive member when the drive voltage is applied to the drive member.

In this configuration, the air bubbles trapped in the liquid chamber can be detected easily with high degree of accuracy. Consequently, such event that the device is continuously used in a state in which the incising or excising capability of the excising device is lowered due to the trapping of the air bubbles can be avoided in advance.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
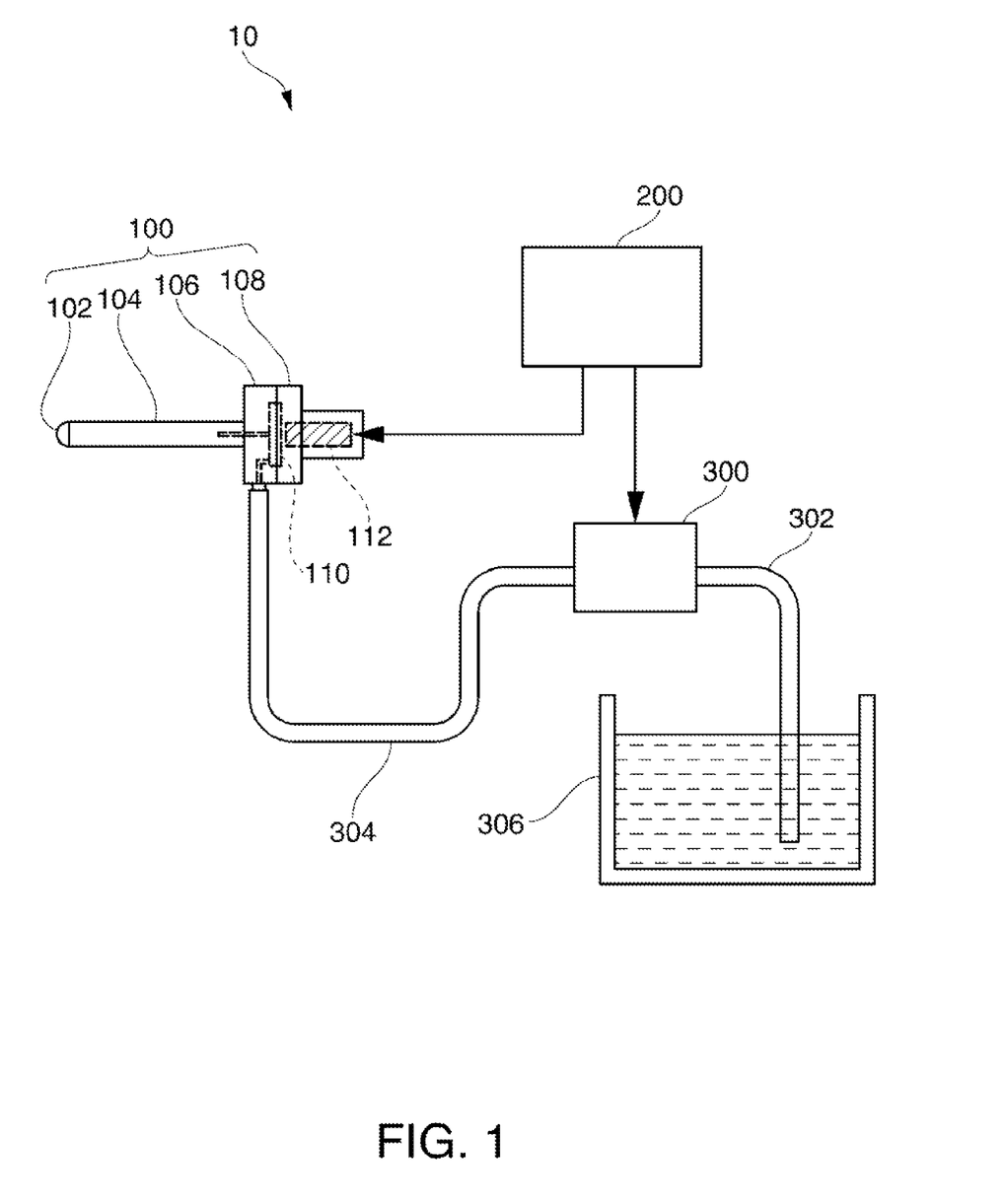
FIG. 1 is an explanatory drawing showing a rough configuration of an excision device according to an embodiment.

In the following description, in order to clarify contents of the invention according to the present application described above, an embodiment will be described in the following order.
A. Configuration of Device
B. Liquid Ejecting Action
C. Principle of Air-Bubble Detection
D. First Example
E. Second Example
F. Modification A. Configuration of Device FIG. 1 is an explanatory drawing showing a rough configuration of an excision device according to an embodiment. An illustrated excision device 10 according to this embodiment roughly includes an ejecting unit 100 configured to eject liquid in a pulsed manner, a supply pump 300 configured to supply liquid to be ejected from the ejecting unit 100 toward the ejecting unit 100, and a control unit 200 configured to control an action of the ejecting unit 100 and the supply pump 300.

The ejecting unit 100 includes a substantially rectangular front block 106 formed of metal and a rear block 108 also formed of metal. The rear block 108 is placed on the rear side of the front block 106 and is secured thereto with a screw. The front block 106 is formed with a circular tube-shaped liquid channel tube 104 on the front surface thereof so as to project therefrom. An ejection nozzle 102 is fitted to a distal end of the liquid channel tube 104. A thin disk-shaped liquid chamber 110 is provided on a mating surface between the front block 106 and the rear block 108. The liquid chamber 110 is connected to the ejection nozzle 102 via a liquid channel tube 104. Provided inside the rear block 108 is an actuator 112 formed of a laminated piezoelectric element. The volume of the liquid chamber 110 can be varied by deforming the liquid chamber 110 by driving the actuator 112.

The supply pump 300 is configured to suck the liquid to be ejected (water, physiologic saline, drug solution, etc.) from a liquid tank 306 having the liquid stored therein via a tube 302, and then supply the liquid into the liquid chamber 110 in the ejecting unit 100 via a tube 304. The control unit 200 controls an action of the excision device 10 by controlling the actuator 112 built in the ejecting unit 100 or the supply pump 300.

Figure 2A:
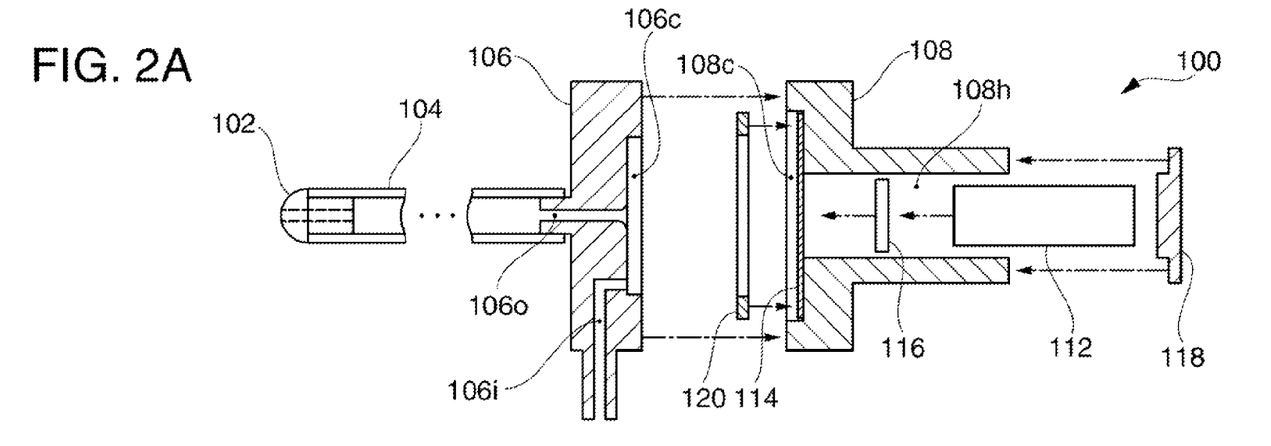
FIGS. 2A and 2B are explanatory drawings showing a configuration of an ejecting unit provided in the excision device according to the embodiment.
Figure 2B:
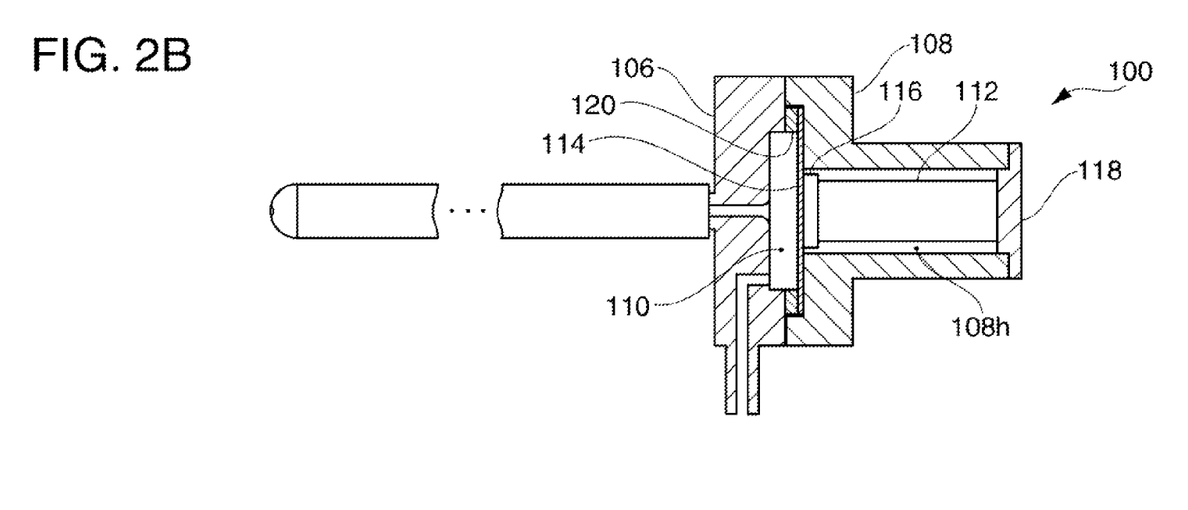

FIGS. 2A and 2B are explanatory drawings showing a detailed structure of the ejecting unit 100. FIG. 2A is an exploded view of the ejecting unit 100 in cross section, and FIG. 2B is a cross-sectional view after assembly. The rear block 108 is formed with a large circular and shallow depression 108c at a substantially center of a mating surface with respect to the front block 106. The depression 108c is formed with a through hole 108h having a circular cross section at a center position thereof so as to penetrate the rear block 108.

Provided on a bottom portion of the depression 108c is a metallic thin diaphragm 114 so as to close the through hole 108h. A peripheral edge portion of the diaphragm 114 is secured to the bottom portion of the depression 108c in an air-tight manner by a method such as brazing or diffusion bonding. An annular shaped metallic reinforcing panel 120 is loosely fitted to the depression 108c from above the diaphragm 114. The thickness of the reinforcing panel 120 is set to a thickness so that an end surface of the rear block 108 formed with the depression 108c and the end surface of the reinforcing panel 120 are flush with each other when the reinforcing panel 120 is fitted from above the diaphragm 114.

The through hole 108h closed by the diaphragm 114 accommodates the actuator 112 (the laminated piezoelectric element in this embodiment), and on the rear side of the actuator 112, the through hole 108h is closed by a disk-shaped metallic bottom panel 118. A circular metallic shim 116 is accommodated between the actuator 112 and the diaphragm 114. The thickness of the shim 116 is selected so that the diaphragm 114, the shim 116, the actuator 112, and the bottom panel 118 come in contact just with each other when the actuator 112 is accommodated in the through hole 108h of the rear block 108 and closing the through hole 108h with the bottom panel 118.

The front block 106 is formed with a circular and shallow depression 106c on the mating surface with respect to the rear block 108. The inner diameter of the depression 106c is set to be almost the same as the inner diameter of the reinforcing panel 120 fitted to the rear block 108. When the front block 106 and the rear block 108 are mated and secured with each other with the screw, the inner peripheral surfaces of the diaphragm 114 and the reinforcing panel 120 provided on the side of the rear block 108 and the depression 106c provided on the front block 106 define a substantially disk-shaped liquid chamber 110.

The front block 106 is provided with a supplying channel 106i for supplying liquid to the liquid chamber 110 from the side of the front block 106. In addition, a small-diameter ejection channel 106o which allows passage of the liquid pressurized in the liquid chamber 110 is penetrated through the depression 106c at the center position thereof. An inner diameter portion of the liquid channel tube 104 is fitted on a portion where the ejection channel 106o opens. Then, the ejection nozzle 102 is fitted on a distal end of the liquid channel tube 104. Therefore, the cross-sectional area of the channel of the liquid ejected from the liquid chamber 110 is configured to be increased in the liquid channel tube 104 after the ejection channel 106o, and then is decreased again in a portion of the ejection nozzle 102 at the distal end of the liquid channel tube 104.

FIG. 2B is a cross-sectional view showing a state in which the ejecting unit 100 is assembled. As illustrated in the drawing, an end surface of the reinforcing panel 120 is flush with an end surface of the rear block 108, and the liquid chamber 110 is defined between the front block 106 and the rear block 108 when mating the front block 106 to this surface. When the shim 116 and the actuator 112 are accommodated in the through hole 108h of the rear block 108 and the bottom panel 118 is mounted, the diaphragm 114, the shim 116, the actuator 112, and the bottom panel 118 come into just contact with each other.

Figure 3:
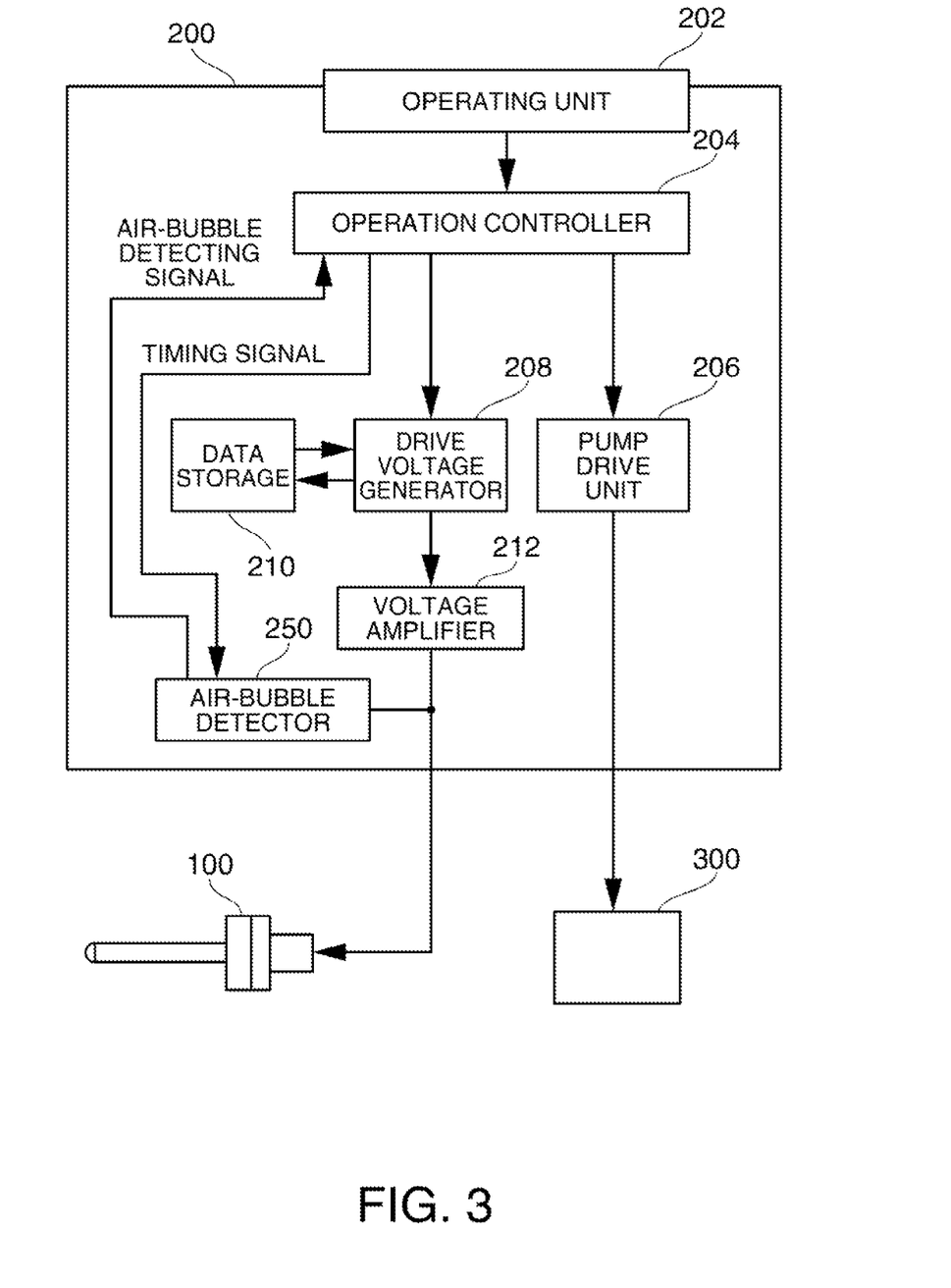
FIG. 3 is an explanatory drawing showing a configuration of a control unit that controls actions of the ejecting unit and a supply pump.

FIG. 3 is an explanatory drawing showing a configuration of the control unit 200 that controls the actions of the ejecting unit 100 and the supply pump 300. As illustrated, the control unit 200 includes an operating unit 202 configured with an operation panel or the like, an action controller 204 configured with a CPU or the like, a pump drive unit 206 that drives the supply pump 300, a drive voltage generator 208 that generates a drive voltage waveform of the actuator 112 under the control of the action controller 204, a data storage 210 having various data for generating the drive voltage waveform stored therein, a voltage amplifier 212 that amplifies the drive voltage waveform generated by the drive voltage generator 208, and an air-bubble detector 250 that detects air bubbles trapped in the ejecting unit 100 by detecting a drive current flowing in the actuator 112 when the drive voltage waveform is applied to the actuator 112 of the ejecting unit 100.

When an operator operates the operating panel of the operating unit 202, a signal is transmitted to the action controller 204, and the action controller 204 outputs a drive command to the pump drive unit 206. Then, the pump drive unit 206 drives the supply pump 300 and, consequently, a supply of liquid into the liquid chamber 110 in the ejecting unit 100 is started. Subsequently, the action controller 204 outputs a drive voltage waveform generation command to the drive voltage generator 208. Then, the drive voltage generator 208 reads out required data from the data storage 210, generates a drive voltage waveform of the actuator 112 built in the ejecting unit 100, and then outputs the generated drive voltage waveform to the voltage amplifier 212. The voltage amplifier 212 amplifies the received voltage value of the drive voltage waveform, and then applies the amplified drive voltage waveform to the actuator 112 of the ejecting unit 100.

Although a detailed configuration of the air-bubble detector 250 will be described later, the air-bubble detector 250 receives a signal (timing signal) which indicates a timing of application of the drive voltage waveform to the actuator 112 from the action controller 204 (or the drive voltage generator 208) and detects the drive current flowing in the actuator 112, thereby detecting the air bubbles trapped in the ejecting unit 100, and outputting a signal indicating the result of detection (air-bubble detecting signal) to the action controller 204. The principle of detection of air bubbles and a detecting method will be described later in detail.

B. Liquid Ejecting Action

Figure 4A:
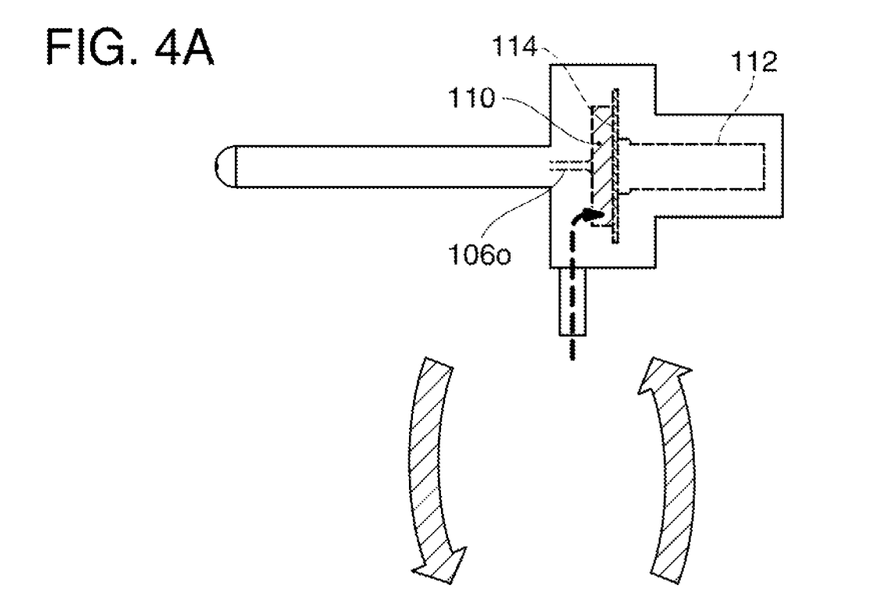
FIGS. 4A and 4B are explanatory drawings showing an action of ejecting liquid performed by the ejecting unit according to the embodiment.
Figure 4B:
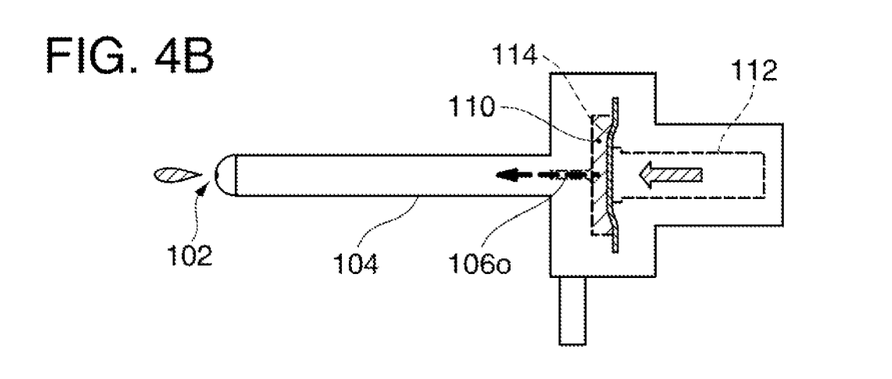

FIGS. 4A and 4B are explanatory drawings showing an action of the ejecting unit 100 ejecting liquid according to the embodiment. FIG. 4A illustrates a state in which the supply pump 300 is driven but the actuator 112 is not driven (a state before application of a driving voltage). In this state, as indicated by a thick broken arrow, the liquid chamber 110 is filled with liquid supplied by the supply pump 300. The drawing indicates that the liquid chamber 110 is filled with the liquid by hatching the liquid chamber 110.

Subsequently, the actuator 112 is driven by applying the drive voltage. Then, the actuator 112 is deformed in the direction of elongation, thereby making an attempt to deform the diaphragm 114 and reduce the volume of the liquid chamber 110. Consequently, the liquid in the liquid chamber 110 is pressurized, and is injected from the ejection nozzle 102 via the ejection channel 106o and the liquid channel tube 104. The volume of the liquid ejected at this time is almost equal to the volume of the liquid chamber 110 reduced by the deformation of the actuator 112.

In addition to the ejection channel 106o, the supplying channel 106i is also connected to the liquid chamber 110. Therefore, the liquid pressurized in the liquid chamber 110 is considered to flow out not only from the ejection channel 106o, but also from the supplying channel 106i. However, actually, the liquid pressurized in the liquid chamber 110 flows out exclusively from the ejection channel 106o, and does not flow out from the supplying channel 106i. The reason will be described below. First of all, since the liquid in the supplying channel 106i attempts to flow into the liquid chamber 110, the flow of the liquid in the supplying channel 106i needs to be pushed backward in order to allow the liquid pressurized in the liquid chamber 110 to flow out from the supplying channel 106i. In addition, since the liquid in the supplying channel 106i is pumped by the supply pump 300, the pressurized liquid must overcome the pressure of the pump as well. In contrast, in the ejection channel 106o, there is no flow of liquid which hinders an outflow from the liquid chamber 110, and the pressure of the supply pump 300 for pumping the liquid does not act in the direction which hinders the outflow from the liquid chamber 110. Therefore, the liquid pressurized in the liquid chamber 110 flows out not from the supplying channel 106i, but exclusively from the ejection channel 106o. In addition, although the description of detailed mechanism is omitted, such configurations that the inner diameter of the channel for the liquid (that is, the inner diameter of the liquid channel tube 104) is increased at a portion just out of the ejection channel 106o and that the length of the ejection channel 106o is shorter than the length of the supplying channel 106i act to facilitate the outflow of the liquid pressurized in the liquid chamber 110 from the ejection channel 106o. From these reasons, the liquid pressurized in the liquid chamber 110 flows out exclusively from the ejection channel 106o, and does not flow out from the supplying channel 106i.

FIG. 4B illustrates a state in which the drive voltage is applied to the actuator 112, and hence the actuator 112 is deformed to reduce the volume of the liquid chamber 110, whereby the liquid is ejected from the ejection nozzle 102 in a pulsed manner by an amount pushed out from the liquid chamber 110.

Here, the expression "to eject pulsed liquid" includes a state of intermittent ejection in which ejection and stop of the liquid are repeated as a matter of course. However, also when the ejection is performed in a state of pulsed flow in which the flow rate and the flow velocity of the liquid vary, the same effect as the case of the intermittent ejection is achieved. Therefore, in this specification, the ejection in the state of pulsed flow is included in the expression "to eject pulsed liquid".

When the pulsed liquid is ejected in this manner, the voltage applied to the actuator 112 is removed. Then, the deformed actuator 112 is restored to the original length and the volume of the liquid chamber 110 reduced correspondingly is restored to the original volume. With this movement, the liquid is supplied from the supply pump 300 to the liquid chamber 110 and, consequently, the actuator 112 shown in FIG. 4A is restored to the state before being driven. When the drive voltage is applied to the actuator 112 from this state again, the actuator 112 is deformed as shown in FIG. 4B, whereby the liquid is ejected from the ejection nozzle 102 in a pulsed manner by an amount pushed out from the liquid chamber 110. In this manner, in the excision device 10 in this embodiment, every time the drive voltage is applied to the actuator 112, the pulsed liquid can be ejected from the ejection nozzle 102.

Since the pulsed liquid is ejected using the mechanism as described above, if the air bubbles get into the liquid chamber 110, when the volume of the liquid chamber 110 is reduced by driving the actuator 112, the air bubbles are crushed. Consequently, the liquid cannot be pressurized significantly, so that the flow velocity of the liquid ejected from the ejection nozzle 102 is lowered. Since the amount of liquid to be pushed out from the liquid chamber 110 is reduced by an amount corresponding to the crushed air bubbles, the amount of liquid ejected from the ejection nozzle 102 is also reduced. When a significantly large quantity of air bubbles are trapped in the liquid chamber 110, the flow velocity or the amount of liquid ejected from the ejection nozzle 102 is significantly reduced, and hence the operator can recognize it immediately. The flow velocity or the amount of liquid ejected from the ejection nozzle 102 can be restored to the normal state by discharging the air bubbles by operating the supply pump 300 for a while without driving the actuator 112, for example. However, if the quantity of the air bubbles trapped in the liquid chamber 110 is not too large, such an event that the operator continues to use the device without recognizing that the flow velocity or the amount of liquid ejected from the ejection nozzle 102 is lowered may occur. Therefore, in order to avoid such event as described above, the excision device 10 in this embodiment is configured to detect the air bubbles trapped in the ejecting unit 100 in a manner described below.

C. Principle of Air-Bubble Detection

Figure 5A:
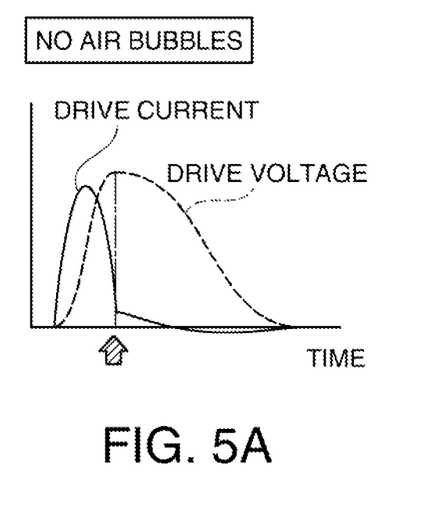
FIGS. 5A and 5B are explanatory drawings showing a principle that the excision device according to the embodiment detects air babbles trapped in the ejecting unit.
Figure 5B:
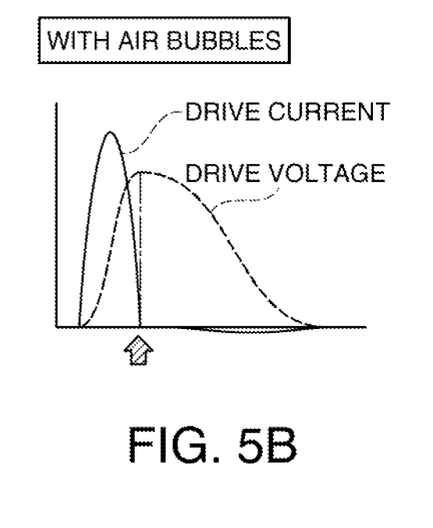

FIGS. 5A and 5B are explanatory drawings showing a principle that the excision device 10 in this embodiment detects the air babbles trapped in the ejecting unit 100. In FIGS. 5A and 5B, a current waveform of a drive current flowing in the actuator 112 when a drive voltage waveform is applied to the actuator 112 is shown. FIG. 5A shows a current waveform when the air bubbles are not trapped in the ejecting unit 100, and FIG. 5B shows a current waveform when the air bubbles are trapped in the ejecting unit 100. In any cases, the same drive voltage waveform is applied to the actuator 112.

First of all, the drive voltage waveform applied to the actuator 112 will be described. The drive voltage waveform of this embodiment employs a voltage waveform generated by combining two sinusoidal waveforms. In other words, part of the waveform where the voltage value rises from voltage 0 to a maximum voltage is configured with a monotonously increasing portion of the sinusoidal waveform (the angular range: part from $-\pi/2$ to $\pi/2$), and part of the waveform where the voltage value is lowered from the maximum voltage to the voltage 0 is configured with a monotonously decreasing portion of the sinusoidal waveform (the angular range: part from $\pi/2$ to $3\pi/2$). The drive voltage waveform configured in this manner has a waveform in which the voltage value rises smoothly from the voltage 0 to the maximum voltage and lowers smoothly from the maximum voltage to the voltage 0. Therefore, the actuator 112 can be deformed smoothly.

The period required for lowering the voltage value from the maximum voltage to the voltage 0 is set to be several times (on the order of five times) longer than the period required for rising the voltage value from the voltage 0 to the maximum voltage. The actuator 112 is deformed in the elongating direction when the voltage value to be applied rises (the direction to reduce the volume of the liquid chamber 110), and is deformed in the shortening direction when the voltage value to be applied is lowered (the direction to increase the volume of the liquid chamber 110). Therefore, by applying the drive voltage waveform as described above to the actuator 112, the volume of the liquid chamber 110 can be reduced in a short time, and then restored to the original volume slowly using a period on the order of five times the period of reduction.

If the liquid chamber 110 is filled with liquid at this time, the actuator 112 receives a reaction force from the liquid chamber 110. The actuator 112 is configured with the piezoelectric element having an electrostrictive effect such as the piezo element. Therefore, a back electromotive force according to the reaction force is generated in the actuator 112. Consequently, an electric current determined by the drive voltage waveform to be applied and the back electromotive force according to the reaction force from the liquid chamber 110 flows into the actuator 112. As a matter of course, the reaction forces that the actuator 112 receives are different between a case where the air bubbles are trapped in the liquid chamber 110 and a case where the air bubbles are not trapped in the liquid chamber 110. Therefore, the generated back electromotive forces are also different, and the electric currents flowing into the actuator 112 are also different.

Actually, when the current (drive current) flowing into the actuator 112 is detected, the current waveforms to be obtained are different between the case where the air bubbles are not trapped in the liquid chamber 110 and the case where the air bubbles are trapped in the liquid chamber 110. Accordingly, determination of the presence or absence of the trapped air bubbles is enabled from the difference in current waveform by detecting the drive current flowing into the actuator 112. The excision device 10 in this embodiment detects the air bubbles trapped in the ejecting unit 100 (the liquid chamber 110, the supplying channel 106i, the ejection channel 106o) on the basis of the principle as described above.

In the description in this specification, the laminated piezoelectric element is used as the actuator 112. However, the same phenomenon may occur also when a solenoid or the like is used as the actuator 112. Then, when the air bubbles are trapped in the liquid chamber 110, the volume of the liquid chamber 110 is quickly reduced because the air bubbles are crushed, and a drive shaft provided at a center of the solenoid is quickly moved. Consequently, the velocity of variations in magnetic flux density passing through a coil provided in the periphery of the drive shaft is increased, and an induced electromotive force is generated in the coil, whereby the waveform of the electric current (drive current) flowing in the actuator 112 varies. In this manner, even when the actuator 112 is configured of members other than the laminated piezoelectric element, the similar phenomenon may occur. Therefore, the presence or absence of the air bubbles trapped in the liquid chamber 110 (or the ejecting unit 100) can be detected by detecting the drive current of the actuator 112.

The difference in drive current waveform flowing into the actuator 112 may be detected by any method. However, the difference in current waveform can be detected easily by focusing on the following points. In other words, when the current waveform when the air bubbles are not trapped as shown in FIG. 5A and the current waveform when the air bubbles are trapped as shown in FIG. 5B are compared, the peak current value rises when the air bubbles are trapped. Therefore, the difference in drive current waveform can be detected immediately by detecting the peak current value. The current value at a timing when the drive voltage waveform is turned from rising to lowering is lowered by the air bubbles trapped therein. Therefore, the difference in drive current waveform can also be detected immediately by detecting the current value at this timing. The method of detecting the trapped air bubbles will be described in detail while focusing on the point described above.

D. First Example

Figure 6:
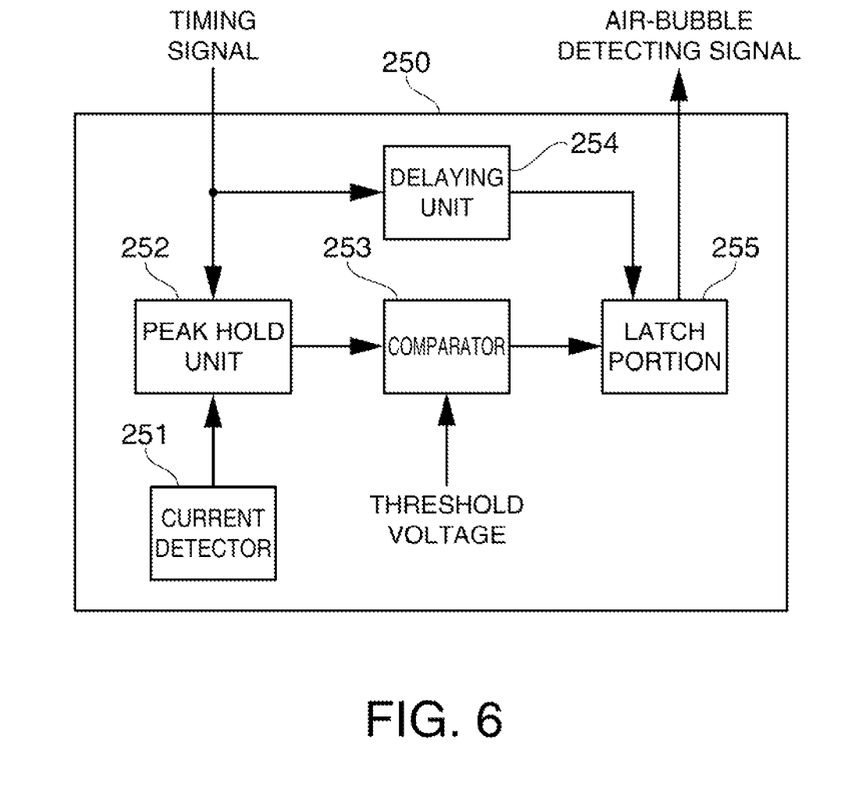
FIG. 6 is an explanatory drawing showing an internal configuration of an air-bubble detector according to a first example.

FIG. 6 is an explanatory drawing showing an internal configuration of an air-bubble detector 250 according to a first example. As illustrated, the air-bubble detector 250 in the first example includes electric circuits such as a current detector 251, a peak hold unit 252, a comparator 253, a delaying unit 254, and a latch portion 255. The current detector 251 is configured mainly with a coil. When an electric current flows toward the actuator 112, an induced electromotive force is generated in the coil, and hence the voltage according to the current value is generated. The voltage generated in this manner is output to the peak hold unit 252. Since the peak hold unit 252 is configured mainly with an IC chip, and has a function to hold the maximum value from the voltage values input thereto. The peak hold unit 252 is configured to receive an input of a timing signal from the action controller 204 (or the drive voltage generator 208), and reset the held voltage value upon receipt of the timing signal.

An output from the peak hold unit 252 (the held maximum voltage) is input to the comparator 253. The comparator 253 is also configured mainly with an IC chip, and has a function to compare the input voltage with a preset threshold voltage and, according to the result of comparison, output a voltage state of either "Hi" or "Low". In this example, when the voltage input from the peak hold unit 252 is larger than the threshold voltage, the voltage state of "Hi" is output, while when input voltage is smaller than the threshold voltage, the voltage state of "Low" is output.

An output from the comparator 253 is input to the latch portion 255. The latch portion 255 is also configured mainly with an IC chip, and has a function to output the voltage value input upon receipt of a latch signal and update the output voltage every time when receiving the latch signal. The latch signal is generated by delaying the above-described timing signal by the delaying unit 254. If the latch portion 255 had already received the voltage of "Hi" state from the comparator 253 when receiving the latch signal, the voltage in "Hi" state is output to the action controller 204 as the air-bubble detecting signal. If the latch portion 255 had already received the voltage of "Low" state from the comparator 253 when receiving the latch signal, the voltage in "Low" state is output to the action controller 204 as the air-bubble detecting signal.

Figure 7:
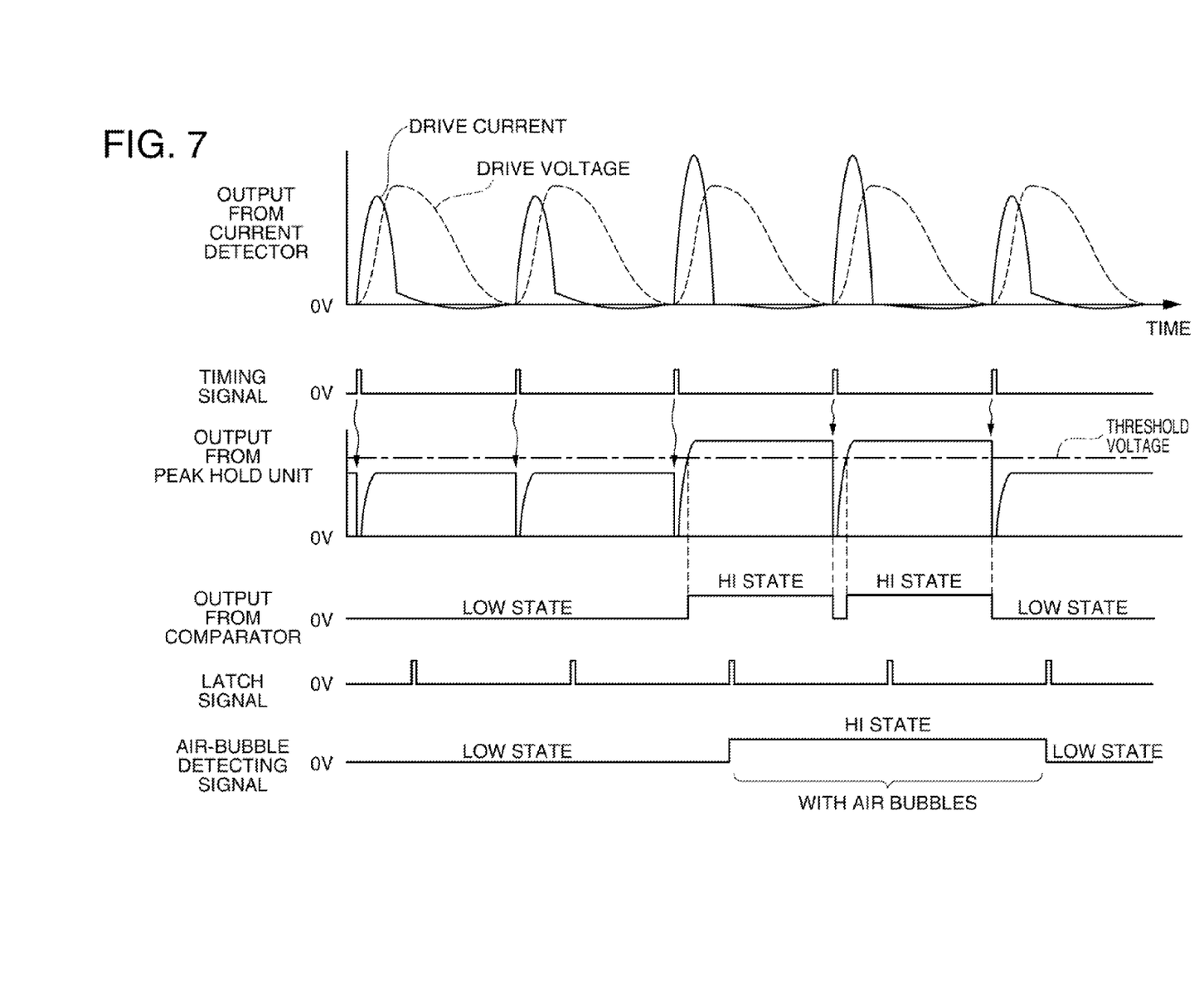
FIG. 7 is an explanatory drawing showing a state in which the air-bubble detector in the first example detects air bubbles.

FIG. 7 is an explanatory drawing showing a state in which the air-bubble detector 250 in the first example detects air bubbles. In an uppermost level in FIG. 7, the drive voltage waveform to be applied to the actuator 112, and a drive current waveform flowing in the actuator 112 thereby are shown. In the illustrated example, the drive voltage waveform is applied five times continuously to the actuator 112, and the drive current waveforms flowing the five times into the actuator 112 every time when the drive voltage waveform is applied are shown. Among these drive current waveforms, first two and the last waveforms are drive current waveforms which appear when the air bubbles are not trapped in the liquid chamber 110 (see FIG. 5A), and the third and fourth waveforms are the drive current waveforms which appear when the air bubbles are trapped (see FIG. 5B).

On the underside of the drive current waveforms, the timing signal output from the action controller 204 (or the drive voltage generator 208) is shown. In the illustrated example, the timing signal is output at timings when the application of the drive voltage waveform to the actuator 112 is started.

An output waveform from the peak hold unit 252 is shown underside of the timing signal. The output from the peak hold unit 252 is reset to a voltage 0 when the timing signal is input, and then rises with the output voltage from the current detector 251 rising. However, even when the output voltage from the current detector 251 is turned to be lowered, the output voltage from the peak hold unit 252 is not lowered, and the maximum output voltage is maintained. When the timing signal is input, the voltage is reset to zero again. As described above, since the timing signal is output at timings of application of the drive voltage waveform to the actuator 112, the output waveform from the peak hold unit 252 indicates a state in which the peak value of the drive current flowing in the actuator 112 varies every time when the drive voltage waveform is applied. In the example shown in FIG. 7, from among the five times of driving of the actuator 112, the output voltage from the peak hold unit 252 is low when the actuator 112 is driven for the first and second times and the last time, and the output voltage from the peak hold unit 252 is high when the actuator 112 is driven for the third time and the fourth time.

The magnitude relationships between the output waveforms from the peak hold unit 252 obtained in this manner and the preset threshold voltage are detected using the comparator 253. In FIG. 7, the threshold voltage for comparing with the output waveforms from the peak hold unit 252 is indicated by an alternate long and short dash line. The output waveform from the comparator 253 is shown on the underside of the output waveform from the peak hold unit 252. As illustrated, when the output voltage from the peak hold unit 252 is lower than the threshold voltage, the output from the comparator 253 is brought into "Low" state. In contrast, when the output voltage from the peak hold unit 252 is higher than the threshold voltage, the output from the comparator 253 is brought into "Hi" state. In the example shown in FIG. 7, from among the five times of driving of the actuator 112, the output from the comparator 253 is brought into "Low" state when the actuator 112 is driven for the first and second times and the last time, and the output from the comparator 253 is brought into "Hi" state when the actuator 112 is driven for the third time and the fourth time.

Every time when the latch portion 255 receives the output from the comparator 253 and receives an input of the latch signal, the latch portion 255 outputs the voltage state (either one of "Low state and "Hi" state) being output from the comparator 253 at that timing as an air bubble detecting signal. In FIG. 7, the latch signal is illustrated underside of the output waveform from the comparator 253, and the air bubble detecting signal output from the latch portion 255 is illustrated under side of the latch signal. Consequently, the air bubble detecting signal is brought into "Hi" state from the third time driving to the fourth time driving from among the five times driving of the actuator 112, so that the fact that the air bubbles are trapped in the liquid chamber 110 is detected.

In this manner, in the air-bubble detector 250 in the first example, the presence or absence of the air bubbles trapped in the liquid chamber 110 (or in the ejecting unit 100) can be quickly and reliably, and very easily detected by detecting the peak value of the drive current when the actuator 112 is driven. Consequently, such event that the operator of the excision device 10 continues to use the excision device 10 without recognizing the fact that the air bubbles are trapped in the ejecting unit 100 or the fact that the incising capability or the excising capability is lowered can be avoided.

E. Second Example

In the first example described above, the air bubbles trapped in the ejecting unit 100 are detected on the basis of the peak value of the drive current when the actuator 112 is driven. However, as described above in conjunction with FIGS. 5A and 5B, the variations of the drive current waveform caused by the presence or absence of the trapped air bubbles appear not only in the peak current value, but also the presence or absence of the trapped air bubbles can be detected by detecting the variations in drive current waveform while focusing on a different point. As described above in conjunction with FIGS. 5A and 5B, when the air bubbles get into the ejecting unit 100, the current value at a timing when the drive voltage waveform applied to the actuator 112 is turned from rising to lowering. A second example in which the air bubbles are detected focusing on this point will be described below.

Figure 8:
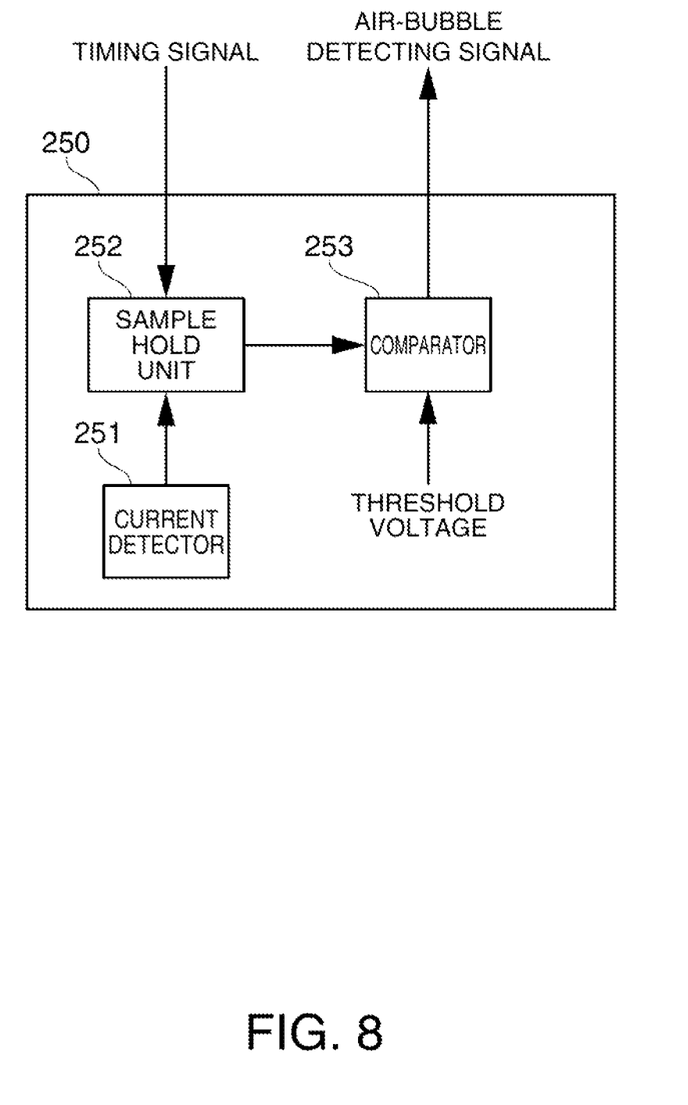
FIG. 8 is an explanatory drawing showing an internal configuration of the air-bubble detector according to a second example.

FIG. 8 is an explanatory drawing showing an internal configuration of the air-bubble detector 250 according to the second example. As illustrated, the air-bubble detector 250 in the second example includes electric circuits such as the current detector 251, a sample hold unit 256, and the comparator 253. From among these members, the current detector 251 is the same as that used in the first example. When an electric current flows toward the actuator 112, the current detector 251 generates a voltage according to the current value and outputs the generated voltage to the sample hold unit 256. The sample hold unit 256 is also configured mainly with an IC chip, and has a function to hold a voltage being input at the time point of reception of the timing signal until reception of a next timing signal. In the second example as well, the timing signal is output from the action controller 204 (or the drive voltage generator 208).

An output from the sample hold unit 256 is input to the comparator 253. The comparator 253 is also the same as that used in the first example, and has a function to compare the input voltage with the preset threshold voltage and, according to the result of comparison, output the voltage state of either "Hi" or "Low". In the second example, when the voltage input from the sample hold unit 256 is smaller than the threshold voltage, the voltage state of "Low" is output, while when the input voltage is larger than the threshold voltage, the voltage state of "Hi" is output. In the second example, the output from the comparator 253 obtained in this manner is used as the air-bubble detecting signal.

Figure 9:
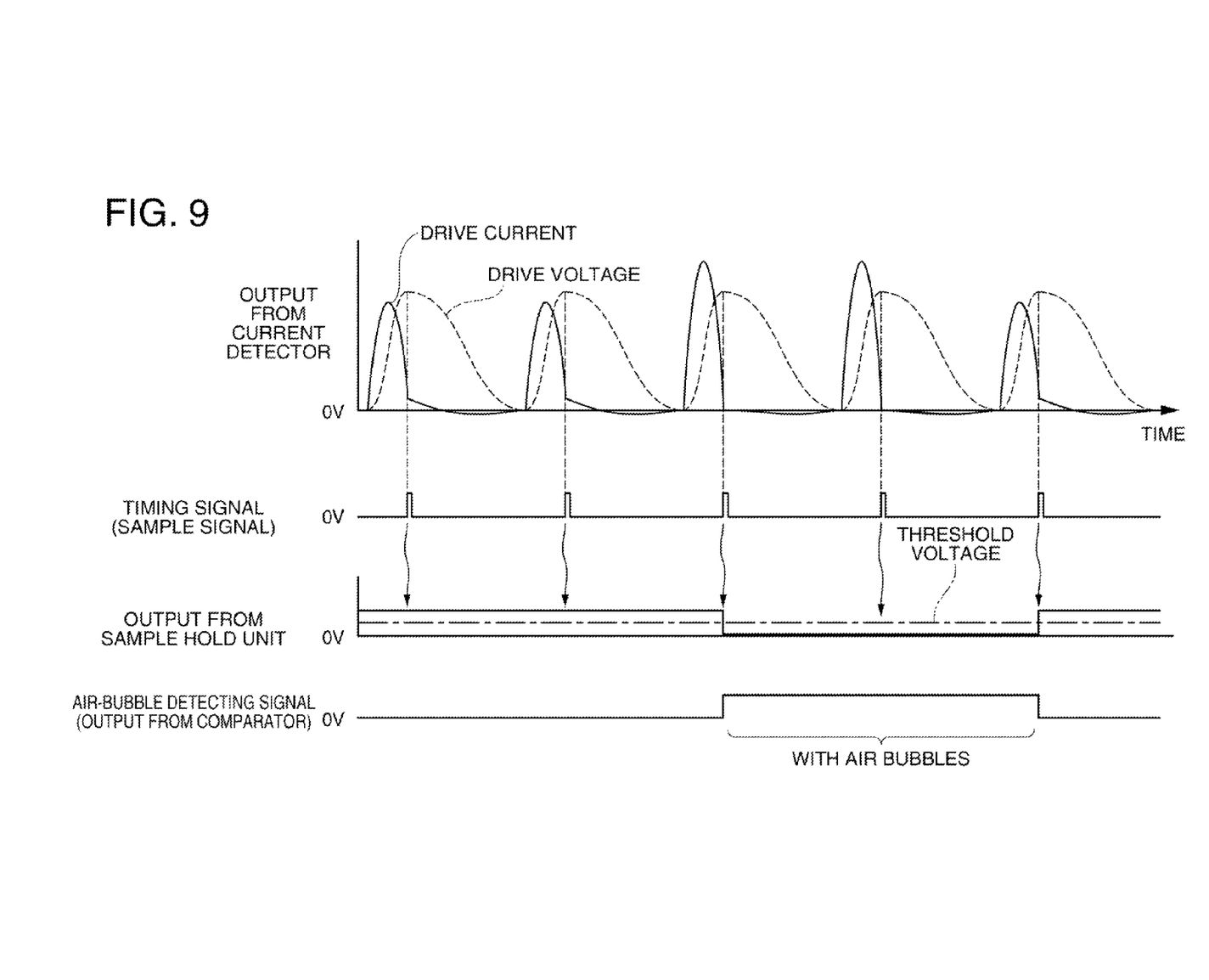
FIG. 9 is an explanatory drawing showing a state in which the air-bubble detector in the second example detects air bubbles.

FIG. 9 is an explanatory drawing showing a state in which the air-bubble detector 250 in the second example detects air bubbles. In the same manner as the first example described above in conjunction with FIG. 7, the drive voltage waveform to be applied to the actuator 112, and the drive current waveform flowing in the actuator 112 thereby are shown also in an uppermost level in FIG. 9. In FIG. 9 as well, first two and the last waveforms from among the five drive voltage waveforms are waveforms which appear when the air bubbles are not trapped, and the third and fourth waveforms are waveforms which appear when the air bubbles are trapped.

On the underside of the drive current waveforms, the timing signal output from the action controller 204 (or the drive voltage generator 208) is shown. In the second example, a timing signal is output at the timings when the drive voltage waveform to be applied to the actuator 112 is turned from rising to lowering.

On the underside of the timing signal, an output waveform from the sample hold unit 256 is shown. As described above, the sample hold unit 256 has a function to output a voltage input from the current detector 251 when receiving the timing signal. Therefore, as shown in FIG. 9, the voltage that the sample hold unit 256 outputs rises for the first two drive current waveforms and the last drive current waveform, and the voltage output from the sample hold unit 256 is lowered for the third and fourth drive current waveforms.

The magnitude relationships between the outputs from the sample hold unit 256 obtained in this manner and the preset threshold voltage are detected using the comparator 253. In FIG. 9 as well, the threshold voltage is shown by an alternate long and short dash line. As shown in FIG. 9, an output from the comparator 253 is brought into "Low" state for the first two drive current waveforms and the last drive current waveform which correspond to the case where the air bubbles are not trapped. The output from the comparator 253 is brought into "Hi" state for the third and fourth drive current waveforms which correspond to the case where the air bubbles are trapped. Therefore, also by using the output from the comparator 253 as the air-bubble detecting signal, the trapping of the air bubbles can be detected quickly and easily. Consequently, such event that the operator of the excision device 10 continues to use the excision device 10 without recognizing the fact that the air bubbles are trapped in the ejecting unit 100 or the fact that the incising capability or the excising capability is lowered is reliably avoided.

F. Modification

In the description of the first example and the second example described above, the threshold voltage used for detecting the air bubbles in the air-bubble detector 250 is fixed. However, the drive current waveforms flowing in the actuator 112 when the air bubbles are trapped are different from one actuator 112 to another. Therefore, the optimal values of the threshold voltage used for detecting the air bubbles are different from one actuator 112 to another. Therefore, the value of the threshold voltage may be varied depending on the individual difference of the actuator 112.

Figure 10:
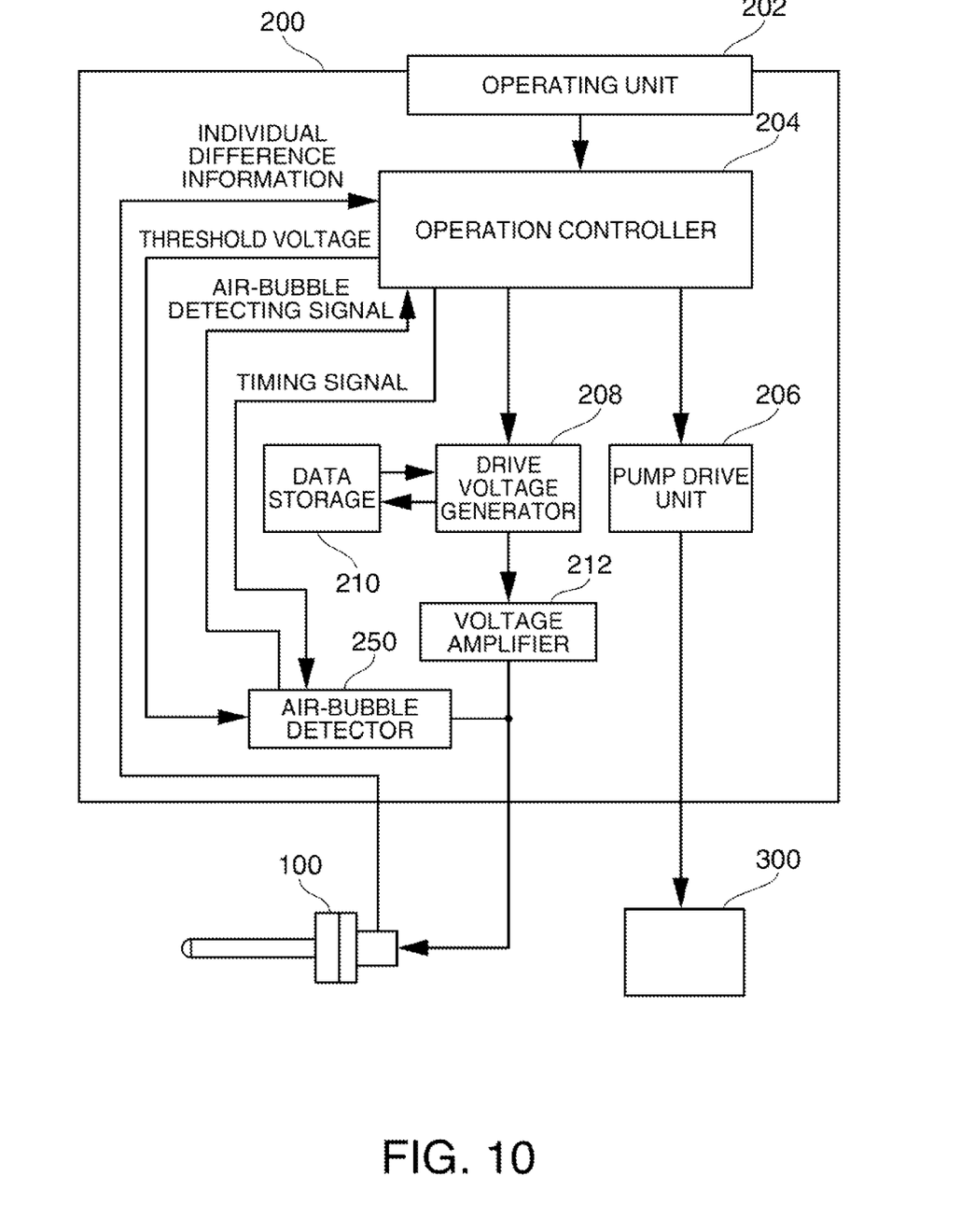
FIG. 10 is an explanatory drawing showing a configuration of the control unit according to a modification.

FIG. 10 is an explanatory drawing showing a configuration of the control unit 200 according to a modification. The control unit 200 in the modification is different from the control units 200 in the first example and the second example described above in conjunction with FIG. 3 in that the action controller 204 obtains the individual difference information of the actuator 112 from the ejecting unit 100 and in that the action controller 204 sets the threshold voltage of the air-bubble detector 250. The individual difference information of the actuator 112 here means data relating to the current value at the timing when the peak current value or the drive voltage turns from rising to lowering obtained by actually measuring the drive current waveform when the air bubbles get into the ejecting unit 100. An IC chip having the individual difference information of the actuator 112 stored therein is mounted on the ejecting unit 100, and the action controller 204 of the control unit 200 is capable of reading out data stored in the IC chip and obtaining the individual difference information of the actuator 112.

The individual difference information of the actuator 112 may be a current value at a timing when the peak current values or the drive voltage is turned from rising to lowering or may be a correcting value determined on the basis of the current value. Alternatively, it may be the number which indicates the types that the actuators 112 are classified into several types on the basis of the measured current values.

In the modification as well, upon receipt of the signal from the operating unit 202, the action controller 204 outputs a drive command to the pump drive unit 206 and drives the supply pump 300, and also outputs a drive voltage waveform generation command to the drive voltage generator 208 to start driving the actuator 112 integrated in the ejecting unit 100. In this manner, since a series of actions performed for ejecting liquid from the ejecting unit 100 is completely the same as in the first and second examples described above, the description will be omitted here.

However, in the modification, the actions for detecting the air bubbles are slightly different from the above-described first embodiment and the second embodiment. In other words, in the modification, the action controller 204 obtains the individual difference information of the actuator 112 from the ejecting unit 100. After having determined the threshold voltage according to the obtained individual difference information, the result is output to the air-bubble detector 250. The action controller 204 may set the threshold voltage for the air-bubble detector 250 by outputting the value of the threshold voltage or by storing a standard threshold voltage in the air-bubble detector 250 and outputting the correcting value of the threshold value. Alternatively, storing a plurality of threshold voltages in the air-bubble detector 250 and specifying one of the stored threshold voltages are also applicable. The air-bubble detector 250 in the modification detects the presence or absence of the air bubbles by comparing the threshold voltage set in this manner and the output from the peak hold unit 252 or the output from the sample hold unit 256.

Accordingly, the presence and absence of the air bubbles can be detected using an adequate threshold voltage considering the individual difference of the actuator 112. Therefore, even when a small quantity of air bubbles are trapped, quick and accurate detection of the trapping of the air bubbles are achieved without being affected by the individual difference of the actuator 112.

In the description of the modification described above, the threshold voltage is varied according to the individual difference of the actuator 112. However, the threshold voltage may be varied according to the drive voltage waveform applied to the actuator 112.

Although the excision device in this embodiment has been descried, the invention is not limited to all of the examples and the modifications described above, and various modes may be implemented without departing from the scope of the invention.

What is claimed is:

1. An excision device configured to excise living tissue by ejecting liquid from an ejection nozzle toward the living tissue comprising:
   a liquid chamber configured to be connected to the ejection nozzle and filled with liquid;
   a drive member configured to vary a volume of the liquid chamber when a drive voltage is applied, wherein the drive member includes a piezoelectric actuator;
   a controller configured to apply the drive voltage to the drive member; and
   an air-bubble detecting unit located separately from the liquid chamber and configured to detect an air bubble in the liquid chamber by detecting an electric current flowing in the drive member when the drive voltage is applied to the drive member,
   wherein the air-bubble detecting unit detects an air bubble in the liquid chamber by using a value of the electric current at a timing where the drive voltage is changed from rising to lowering,
   wherein an absolute value of the electric current at a timing where the drive voltage is changed from rising to lowering when an air bubble is present is smaller than that of when an air bubble is not present.

2. The excision device according to claim 1, wherein the value of the electric current at a timing where the drive voltage is changed from rising to lowering differs from a peak electric current.

3. The excision device according to claim 2, wherein the absolute value of the electric current at a timing where the drive voltage is changed from rising to lowering when air bubble is present is nearly zero.

4. The excision device according to claim 1, wherein the controller applies a voltage having a waveform rising to a predetermined maximum voltage and then lowering from the maximum voltage to the drive member, and the air-bubble detecting unit detects the air bubble when the maximum voltage is applied to the drive member.

5. The excision device according to claim 1, further comprising:
a storage unit that stores a reference current according to the drive member,
wherein the air-bubble detecting unit detects the air bubble in the liquid chamber by comparing the electric current flowing in the drive member with the reference current.

6. The excision device according to claim 1, wherein the air-bubble detecting unit includes a comparator, the comparator outputting a low state signal when an air bubble is not present in the liquid chamber and outputting a high state signal when an air bubble is present in the liquid chamber.

* * * * *